United States Patent [19]

House

[11] Patent Number: 5,236,108
[45] Date of Patent: Aug. 17, 1993

[54] MULTIPLE-BARREL DISPENSING CONTAINER ASSEMBLY WITH INDUCTION SEAL

[75] Inventor: Eugene R. House, Maplewood, Minn.

[73] Assignee: Minnesota Mining and Manufacturing Company, St. Paul, Minn.

[21] Appl. No.: 763,671

[22] Filed: Sep. 25, 1991

[51] Int. Cl.⁵ .......................................... B65D 47/10
[52] U.S. Cl. ..................... 222/541; 222/137; 222/545; 215/322; 215/341; 215/347; 220/345; 220/351
[58] Field of Search .............. 215/232, 322, 341, 347, 215/349; 222/562, 545, 541, 542, 137, 145, 136, 135, 94; 220/345, 351

[56] References Cited

U.S. PATENT DOCUMENTS

| | | | |
|---|---|---|---|
| 1,349,511 | 8/1920 | Kandlbinder | 215/322 X |
| 2,436,297 | 2/1948 | Guarnaschelli | 215/322 |
| 2,661,870 | 12/1953 | Huenergardt | 222/94 X |
| 2,826,339 | 3/1958 | Maillard | 222/137 |
| 3,105,615 | 10/1963 | Koga | 222/145 X |
| 3,197,071 | 7/1965 | Kuster | 222/145 X |
| 3,323,682 | 6/1967 | Geighton, Jr. et al. | 222/94 |
| 3,443,726 | 5/1969 | Muller et al. | 222/80 |
| 3,506,157 | 4/1970 | Dukess | 222/94 |
| 3,782,600 | 1/1974 | Columbus | 222/94 |
| 3,928,109 | 12/1975 | Pollock et al. | 156/272 |
| 4,121,739 | 10/1978 | Devaney et al. | 222/137 |
| 4,396,655 | 8/1983 | Graham et al. | 428/35 |
| 4,418,834 | 12/1983 | Helms et al. | 215/232 X |
| 4,538,920 | 9/1985 | Drake | 366/177 |
| 4,570,826 | 2/1986 | Fattori | 222/83 |
| 4,583,665 | 4/1986 | Barriac | 222/83 |
| 4,747,500 | 5/1988 | Gach et al. | 215/349 X |
| 4,771,919 | 9/1988 | Ernst | 222/145 X |
| 4,801,008 | 1/1989 | Rich | 206/219 |
| 4,869,399 | 9/1989 | Dubach | 222/83 |
| 4,872,571 | 10/1989 | Crecelius et al. | 222/541 X |
| 4,964,539 | 10/1990 | Mueller | 222/94 |
| 4,974,756 | 12/1990 | Pearson et al. | 222/562 |
| 4,989,758 | 2/1991 | Keller | 222/137 |
| 4,995,540 | 2/1991 | Colin et al. | 222/132 |
| 5,020,694 | 6/1991 | Pettengill | 222/545 X |
| 5,033,650 | 7/1991 | Colin et al. | 222/137 |
| 5,052,590 | 10/1991 | Ratcliff | 222/94 |

OTHER PUBLICATIONS

Brochure from Enercon Industries Corporation, Menomonee Falls, WI.
3M Brochure No. 70-2008-4492-9 (copyright 199) 3M Company, St. Paul, MN.

Primary Examiner—Andres Kashnikow
Assistant Examiner—Anthoula Pomrening
Attorney, Agent, or Firm—Gary L. Griswold; Walter N. Kirn; James D. Christoff

[57] ABSTRACT

A dispensing assembly includes a seal that is induction-bonded to an outlet of a container. A cap is detachably connected to the container over the seal to protect the seal during shipping. Once the cap is removed, the seal can be peeled away from the outlet. The absence of the seal can be observed when an attempt is made to reconnect the cap to the container after the seal has been removed.

10 Claims, 2 Drawing Sheets

5,236,108

MULTIPLE-BARREL DISPENSING CONTAINER ASSEMBLY WITH INDUCTION SEAL

BACKGROUND OF THE INVENTION

1. Field of the Invention

This invention relates to an assembly that includes a container, a seal extending over an outlet of the container and a cap detachably connected to the container over the seal.

2. Description of the Related Art

Multiple-barrel dispensing containers such as double barrel syringes are useful for storing different reactive components that, once dispensed, are mixed together to form a desired composition. As an example, a double barrel syringe for dispensing dental impressioning material may hold a catalyst component in one chamber and a base component in another chamber. Portions of each impressioning component are simultaneously dispensed for immediate mixing and measuring of the separate components is unnecessary.

One example of a double barrel dispensing syringe is described in U.S. Pat. No. 4,538,920 which is assigned to the assignee of the present invention. The syringe has two interconnected plungers for simultaneously dispensing proportioned amounts of material from each barrel. An exit conduit is releasably connected to the syringe and has a plurality of helical mixing elements so that the components are thoroughly mixed once discharged from the exit conduit and mixing by hand may be avoided.

Typically, only a portion of the components are dispensed at any one time from the barrels of the syringe shown in U.S. Pat. No. 4,538,920, and it is often desirable to keep the side-by-side outlets of the syringe covered between dispensing operations in order to prevent undue hardening or drying of the component materials in the barrels. In the past, certain dispensing syringes have been provided with a cap having flanges that releasably lock into recesses next to the two outlets of the syringe as the cap is turned approximately ninety degrees relative to the syringe. The cap carries an internal seal that covers both of the outlets when coupled to the syringe.

However, many conventional caps for double barrel syringes may contribute to cross-contamination of the remaining materials within the barrels both before and after initial use of the syringe. For example, if a small quantity of material of one barrel is deposited on the seal within the rotatable cap mentioned above, the material may contact and react with material in the other barrel as the cap is re-coupled onto the container after initial use. As another example, the recesses holding the flanges of the rotatable cap may elongate, enabling the migration of material across the seal from one outlet to the other. Although in either example the amount of reacted material and resulting cross-contamination may be relatively small compared to remaining material within the barrels, such cross-contamination may result in a certain amount of polymerization that might hinder passage of the material along the tortuous path presented by the helical mixing elements.

Users of double barrel syringes are often provided with instructions that indicate that good results are attained when the exit conduit with the helical mixing elements is left connected to the container after use and the cap is not re-used. In this manner, mixed material within the exit conduit hardens and provides a seal that is generally more satisfactory than a seal that would be established by re-use of the cap. Immediately prior to the next use, the exit conduit is disposed of and a new exit conduit is connected to the container in its place. Unfortunately, some individuals do not follow the written instructions and attempt to re-use the rotatable cap, possibly leading to the problems mentioned above.

A push-on cap having a protruding orienting section for use with a double barrel dispensing container having a threaded outlet is described in U.S. Pat. No. 4,974,756, assigned to the assignee of the present invention. The orienting section ensures that the cap is in a certain orientation relative to the container each time that the cap is coupled to the container, so that the likelihood of cross-contamination is reduced. However, while the cap described in U.S. Pat. No. 4,974,756 is highly satisfactory for use with many types of materials, there are certain instances where it is desired to discourage re-use of a cap and instead encourage the user to leave the exit conduit in place after a dispensing operation.

SUMMARY OF THE INVENTION

The present invention concerns a multiple-barrel dispensing container assembly that includes a container having a first barrel with a first outlet, and a second barrel with a second outlet in side-by-side relation with the first outlet. The container includes wall structure surrounding the first outlet and the second outlet, and a wall section extends between the first outlet and the second outlet. The wall structure and the wall section have outermost end surfaces. A seal extends over the first outlet, the second outlet and the outermost end surfaces. Means is provided between the seal and the outermost end surfaces for coupling the seal directly to the end surfaces and for enabling the seal to be uncoupled from the end surfaces in peel-off fashion. A cap extends over the seal, and a connector detachably connects the cap to the container, whereby the seal may be accessed.

Uncoupling of the seal in peel-off fashion provides tacit notice to the user that the seal and the accompanying cap are not intended to be reused. The user is thereby encouraged to leave the used exit conduit coupled to the container between uses to provide a seal for remaining material in the barrels. Further, coupling the seal to end surfaces of the wall structure surrounding the outlets and the wall section between the outlets reduces the likelihood of migration of materials from one barrel to another and provides good results even when pressure is exerted against the seal during filling of the barrels by the manufacturer.

The invention is also directed to a dispensing container assembly having a dispensing container with an outlet, a seal extending over the outlet, and means for removably coupling the seal to the container. A cap extends over the seal, and a connector detachably connects the cap to the container. The cap has an overall generally U-shaped configuration with opposed side openings.

DETAILED DESCRIPTION OF THE PREFERRED EMBODIMENT

Figure 4:
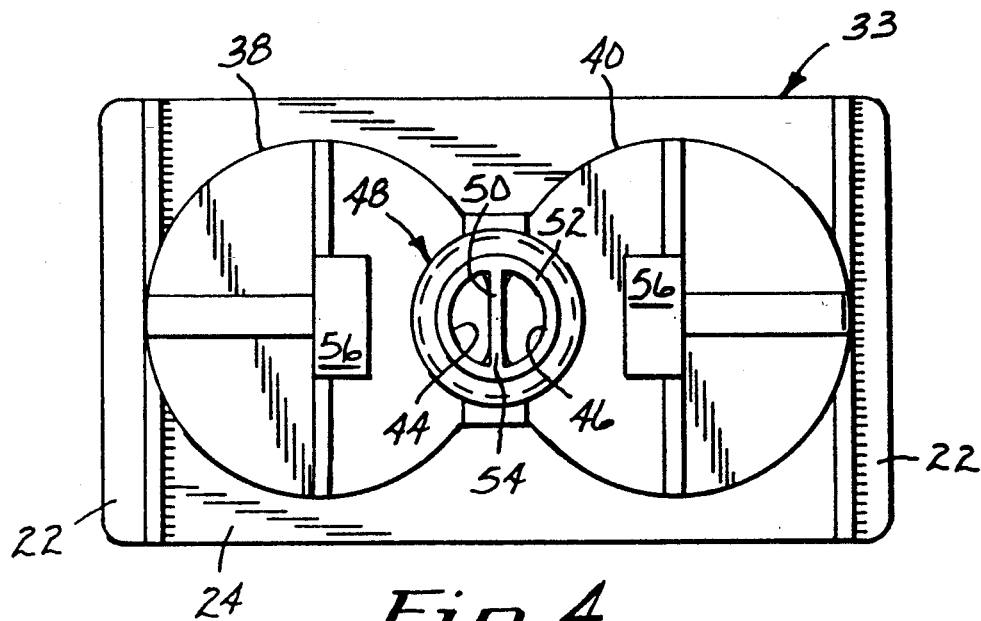
FIG. 4 is a view somewhat similar to FIG. 3 except with the cap and seal removed.
Figure 1:
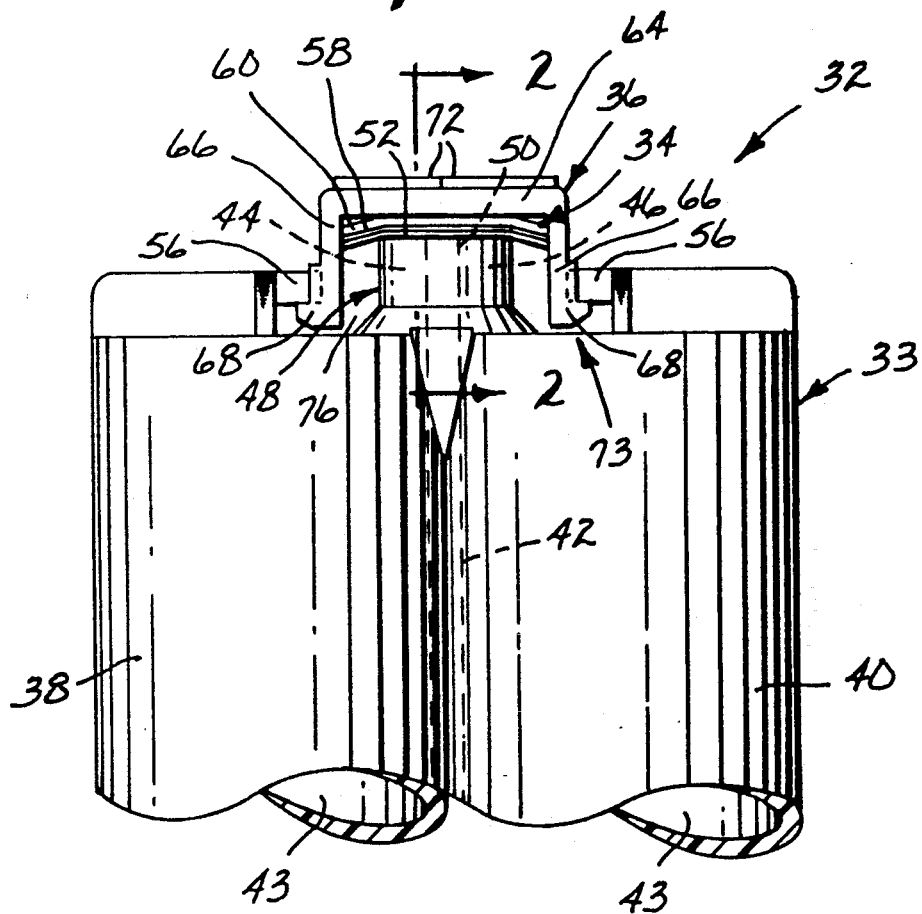
FIG. 1 is a fragmentary plan view of a double barrel dispensing container, cap and seal assembly according to the invention.
Figure 2:
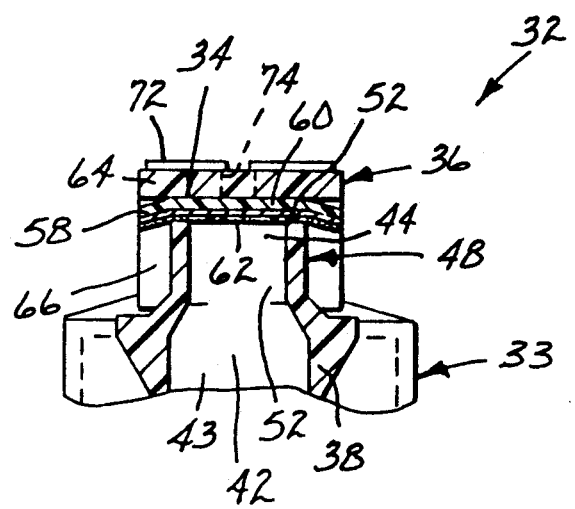
FIG. 2 is a fragmentary, side cross-sectional view taken along line 2—2 of FIG. 1.
Figure 3:
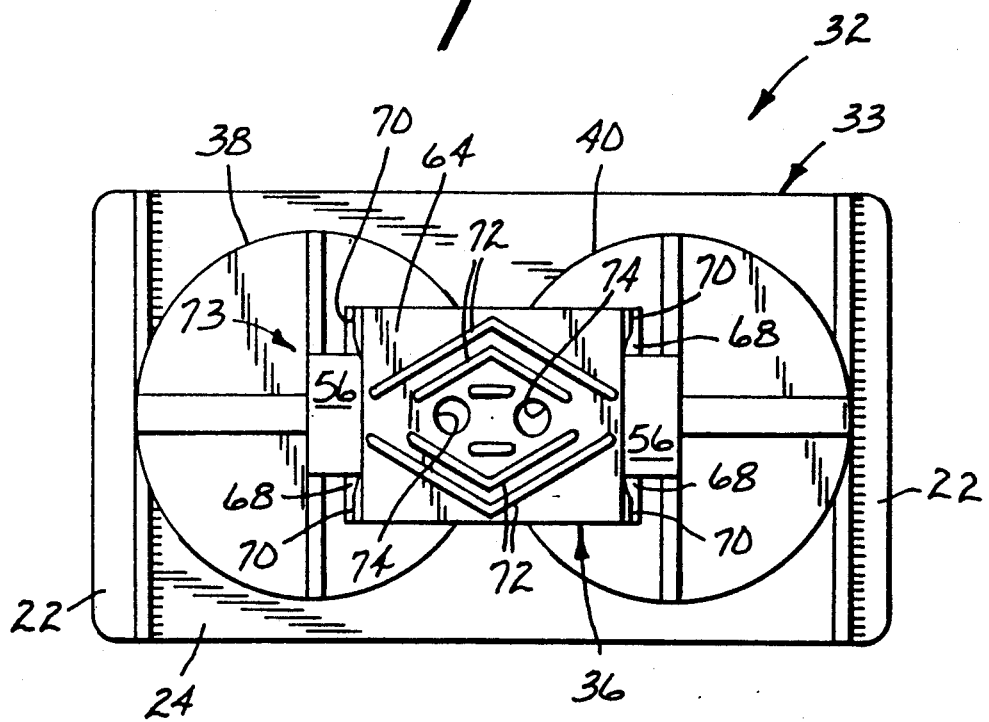
FIG. 3 is an end view of the assembly shown in FIGS. 1 and 2.

A multiple-barrel dispensing container assembly 32 according to the invention is illustrated in FIGS. 1-3 and broadly includes a container 33 as well as a seal 34 and a cap 36. The container 33 alone is shown in FIG. 4. The container 33 includes first and second cylindrical, hollow, juxtaposed barrels 38, 40 that are separated by a wall 42 (FIGS. 1-2). Each barrel 38, 40 has an internal chamber 43 adapted to contain a different component of the mixture to be dispensed.

The forward end of the first barrel 38 has a semi-cylindrical first outlet 44 (FIGS. 1, 2 and 4). The second barrel 40 has a similar, semi-cylindrical second outlet 46 (FIGS. 1 and 4) that is in side-by-side relation to the first outlet 44.

The container 33 has protruding wall structure 48 in the form of a front neck that surrounds the first outlet 44 and the second outlet 46. The wall structure 48 includes a forwardmost cylindrical portion and a frustoconical portion integrally interconnecting the cylindrical portion and the barrels 38, 40. A wall section 50, forming an extension from wall 42, integrally connects opposite sides of the wall structure 48 in bisecting relation and separates the first outlet 44 from the second outlet 46.

The wall structure 48 has an annular, outermost flat end surface 52 that is planar with a flat, outermost end surface 54 of the wall section 50. The surfaces integrally connected 52, 54 extend in a plane perpendicular to the parallel, central, longitudinal axes of the barrels 38, 40.

The forward end of the container 33 includes two rectangular flanges 56 (FIGS. 1, 3 and 4) that extend inwardly toward each other in a direction parallel to the flat end surfaces 52, 54. The flanges 56 are adapted to receive inclined shoulders formed on the rear end of an exit conduit as the exit conduit is placed over the wall structure 48 and turned 90 degrees to couple the exit conduit to the container 33.

The exit conduit includes a plurality of internal, helical mixing elements and is similar to the exit conduit described in U.S. Pat. No. 4,538,920, the disclosure of which is incorporated by reference herein. The container 33 is adapted to couple with a hand-operated dispensing mechanism such as the EXPRESS brand dispenser (Part no. 7308, 3M). The mechanism has a double headed plunger that, when advanced, bears against pistons (not shown) in the container 33 that, in turn, urge materials toward the exit conduit. The helical mixing elements within the exit conduit successively subdivide, rotate and recombine the incoming streams of material. The exit conduit dispenses the thoroughly mixed material through an outlet directly to an application site.

The seal 34 comprises a circular flat sheet 58 (FIGS. 1-2) of aluminum foil and an overlying circular flat sheet 60 of closed cell foam that is bonded to the sheet 58. A layer 62 (FIG. 2) of polyolefin is coated onto the underside of the foil sheet 58 and serves as a means between the seal 34 and the end surfaces 52, 54 for coupling the seal 34 directly to the end surfaces 52, 54 and for enabling the seal 34 to be uncoupled from the end surfaces 52, 54 in peel-off fashion. A preferred seal material is SAFE-GARD brand 108 induction inner seal, No. 70-0703-8951-8, 3M Packaging Systems Division.

The assembly 32 is subjected to induction heating apparatus that directs an electromagnetic field toward the foil sheet 58 and induces eddy currents in the sheet 58 to cause relatively mild, localized heating. The heat fuses the polyolefin layer 62 on the foil sheet 58 to the end surfaces 52, 54, establishing a hermetic seal. As an alternative, an ultrasonic technique, a heated adhesive, a pressure sensitive adhesive or other bonding method may be utilized to releasably fix the seal 34 directly to the end surfaces 52, 54.

The cap 36 has a generally inverted U-shaped configuration (see, e.g., FIG. 1) with a flat top portion 64 and a pair of depending, spaced-apart legs 66. Each leg 66 has an outwardly extending lip 68 that engages a rear surface of the respective flange 56 as depicted in FIG. 1. Additionally, each leg 66 has two spaced-apart tabs 70 as shown in FIG. 3 that straddle the respective flange 56 to facilitate retention of the cap 36 in place as shown in FIGS. 1-3 and inhibit lateral sliding movement of the cap 36 along the underside of the flanges 56. The cap 36 protects the seal 34 during shipping and handling of the container 33.

The top portion 64 of the cap 36 has a series of ridges 72 (see, e.g., FIG. 3) that provide a gripping surface for laterally sliding the cap 36 when desired to remove the cap 36 from the container 33. The cap 36 is integrally molded of polypropylene, and as such is inherently flexible to a limited extent. Intentional urging of the cap 36 in a lateral direction (i.e., in an upward direction viewing FIG. 3) causes the legs 66 to deflect inwardly toward each other as inclined inner edges of one pair of tabs 70 are moved along the flanges 56. Continued lateral movement of the cap 36 causes the cap 36 to disconnect from the container 33. As can be appreciated, the lips 68 together with the flanges 56 comprise a connector 73 for detachably connecting the cap 36 to the container 33, whereby the seal 34 may be accessed.

The cap 36 has two holes 74 (FIGS. 2 and 3) that lie directly over respective outlets 44, 46 when the cap 36 is in the position shown in FIGS. 1-3. If, for instance, an attempt is made to replace the cap 36 on the container 33 after the seal 34 has been removed, the holes 74 function as a vent to communicate the outlets 44, 46 with the atmosphere.

The assembly 32 is constructed to discourage re-use of the cap 36 once the seal 34 has been peeled away by the user, so that the user instead tends to leave the exit conduit in place after a dispensing operation. The exit conduit provides an effective and efficient seal between the outlets 44, 46 and the atmosphere, and moreover is normally discarded before the next dispensing operation because of the difficulty in cleaning the inner confines of the exit conduit. The assembly 32 discourages re-use of the cap 36 by providing means for indicating the absence of the seal 34 if the cap 36 is re-used after the seal 34 has been removed.

One element that indicates the absence of the seal 34 is the space between the cap 36 and the end surfaces 52, 54 that is present after the seal 34 is removed. The space permits the cap 36 to move a limited distance in a vertical direction viewing FIGS. 1 and 2 and enables the cap 36 to rattle, thereby advising the user that only a loose coupling is now provided. The space also provides a noticeable vent between the outlets 44, 46 and the atmosphere when the seal 34 is removed and the cap 36 is re-used.

Other elements that indicate the absence of the seal 34 are the two side openings 76 (one of which is shown in FIG. 1) of the cap 36, in contrast to conventional caps that fully surround a seal. Observation of the openings 76 enables the user to determine whether or not the seal 34 is in place.

Additionally, the holes 74 provide an indication for the absence of the seal 34, especially when the seal 34 is light in color compared to the typically darker color of the materials within the barrels 38, 40. The holes 74 also provide an evident vent between the outlets 44, 46 and the atmosphere when the cap 36 is re-used after the seal 34 has been removed.

The diameter of the seal 34 is larger than the outer diameter of the wall structure 48 and preferably engages the legs 66 to hold the seal 34 in place during assembly. As a consequence, the seal 34 overhangs the wall structure 48 for facilitating grasping by the user after the cap 36 is removed. The induction sealing process for bonding the seal 34 to the end surfaces 52, 54 enables the seal 34 to be readily removed in peel-off fashion from both of the outlets 44, 46 in a single motion without leaving undue amounts of residue on the end surfaces 52, 54 that otherwise might adversely affect subsequent seating of the end surfaces 52, 54 on inner surfaces of the exit conduit. The induction sealing process also does not unduly damage or distort the end surfaces 52, 54.

Furthermore, the induction-bonded polyolefin layer 62 provides an effective barrier between the outlets 44, 46 to avoid undue migration of materials from one outlet to the other, even when the seal 34 is subjected to pressure during filling of the barrels 38, 40. In this regard, the container 33 is made in a mold having gates located outwardly of each flange 56 so that the wall structure 48 and the wall section 50 are positioned in the middle of the mold and the end surfaces 52, 54 are, as a result, relatively smooth and precisely coplanar in order to enhance the bond to the seal 34. To this end, a gas vent is located in the mold facing the wall section 50 and next to the end surface 54.

EXAMPLE

A 11.5 mm diameter seal was punched out of rollstock material (Safe-Gard brand 108 induction inner seal) and was placed into a cap similar to cap 36. The seal and cap were pneumatically placed onto outlet wall structure of a double barrel dispensing syringe container similar to container 33, and the assembly was then positioned next to an induction sealer (Model #1 KW N1, Enercon Industries Corporation). The cap was 6 mm from the electromagnetic head of the induction sealer, and the sealer was activated using a 70% power output and a dwell time of 12 seconds. The seal was observed to remain fixed to the flat end surface of the wall structure as well as a flat end surface of a wall section between the side-by-side outlets during filling of the barrels, and yet cleanly pulled away in a peeling motion from the end surfaces after the cap had been removed.

I claim:

1. A dispensing container assembly comprising:
   a dispensing container having a protruding outlet;
   a peel-off seal removably bonded to said outlet;
   a cap extending over said seal, said cap having an overall generally U-shaped configuration with at least one side opening; and
   a connector detachably connecting said cap to said container, said cap being detachable from said container while said seal remains bonded to said outlet when said cap is moved in a lateral direction relative to said container to move said side opening at least partially across said outlet,
   wherein said cap includes a top portion having a hole exposing said seal to the atmosphere.

2. The assembly of claim 1, wherein said seal includes a sheet of foil and a sheet of film fixed to said sheet of foil.

3. The assembly of claim 1, wherein said connector enables movement of said cap to a limited extent relative to said container when said seal is not present.

4. The assembly of claim 1, wherein said seal is bonded by an induction heating bond to said outlet.

5. The assembly of claim 1, wherein said dispensing container includes a first barrel and a second barrel, and wherein said first barrel includes said outlet, and wherein said second barrel includes a second outlet, and wherein said container includes wall structure surrounding said outlets of said first barrel and said second barrel, said wall structure including outermost end surfaces, and wherein said seal is bonded to said outermost end surfaces.

6. The assembly of claim 5, wherein said seal includes a portion overhanging said wall structure for grasping.

7. The assembly of claim 5, wherein said first barrel and said second barrel have parallel longitudinal axes, and wherein said connector includes a flange having a configuration for enabling said cap to be detached from said container when said cap is moved in a direction laterally of said axes.

8. The assembly of claim 5, wherein said container includes a wall section having an outermost end surface and located between said outlets of said first barrel and said second barrel, and wherein said seal is bonded to said end surface of said wall section.

9. The assembly of claim 8, wherein said end surface of said wall section is planar with said end surfaces of said wall structure.

10. The assembly of claim 9, wherein said wall structure has an annular configuration and said wall section bisects said wall structure.

* * * * *